United States Patent

Gearey et al.

[11] Patent Number: 6,010,889
[45] Date of Patent: Jan. 4, 2000

[54] ELECTROCHEMICAL NOISE MEASUREMENT TO ASSESS CELLULAR BEHAVIOR AND METABOLIC ACTIVITY

[75] Inventors: David Gearey, Sale Moor; David Edward Woolley, Poynton; Robert David Eden, Warrington, all of United Kingdom

[73] Assignee: The University of Manchester Institute of Science and Technology, Manchester, United Kingdom

[21] Appl. No.: 08/817,290
[22] PCT Filed: Sep. 29, 1995
[86] PCT No.: PCT/GB95/02297
  § 371 Date: Jun. 23, 1997
  § 102(e) Date: Jun. 23, 1997
[87] PCT Pub. No.: WO96/10742
  PCT Pub. Date: Apr. 11, 1996

[30] Foreign Application Priority Data

Sep. 30, 1994 [GB] United Kingdom ........... 9419716

[51] Int. Cl.[7] .............. C12N 13/00; C12Q 1/02; G01N 27/26
[52] U.S. Cl. .......... 435/173.1; 435/29; 204/403
[58] Field of Search .................... 435/29, 173.1; 204/403

[56] References Cited

U.S. PATENT DOCUMENTS 5,489,515  2/1996  Hatschek et al. ............ 435/29
5,507,936  4/1996  Hatschek et al. ............ 204/412

FOREIGN PATENT DOCUMENTS 028793   5/1981  European Pat. Off. .
627621  12/1994  European Pat. Off. .

OTHER PUBLICATIONS

Kandel et al. (1981) Principles of Neural Science, Elsevier/North–Holland, New York, p. 74.

Stryer (1988) Biochemistry, 3rd Ed., W.H. Freeman and Co., New York, pp. 1018–1019.

Primary Examiner—Jon P. Weber
Attorney, Agent, or Firm—Akin, Gump, Strauss, Hauer & Feld, LLP

[57] ABSTRACT

A method and apparatus is presented for analyzing directly obtained electrochemical noise measurements at cellular surfaces to assess cellular behavior and metabolic activity. The apparatus comprises a container (1) into which culture medium containing the cells to be assessed (2) has been introduced. Located within the container and partially submerged by the culture medium is a main electrode (3) which is a chemically inert electrically conductive surface such as gold film. This electrically conductive surface supports the adherent, viable cells to be assessed, and which may have been previously grown on the electrode to near confluence. The container is closed by a lid (4) which is penetrated by a tube (5) filled with an electrochemically conducting medium that is in electrochemical contact with a reference electrode. The end of the tube (5) is immersed in the culture medium. A further tube is provided through which test factors such as stimulants or suppressants can be injected into the container as indicated by the arrow. The directly measured electrochemical noise reflects metabolic activity of the cell at the cell surface. Fluctuations in the electrochemical noise are analyzed in the conventional manner and correlated with cellular activity.

15 Claims, 5 Drawing Sheets

ELECTROCHEMICAL NOISE MEASUREMENT TO ASSESS CELLULAR BEHAVIOR AND METABOLIC ACTIVITY

The present invention relates to a method and apparatus for the monitoring of electrochemical signals which reflect the metabolic and behavioural activities of living cells.

All cells utilise metabolic pathways based on chemical processes, for example, the oxidation-reduction reactions of energy metabolism. In addition there are hundreds of other chemical processes, especially the electrochemical reactions and ionic pumps' that cross the cell surface, all of which provide the molecular basis for the cell's behavioural activities.

It is well known that cells are electrochemically active, and that changes in energy metabolism often relate to modified cell behaviour. For example, the article "The Cytosensor Microphysiometer: Biological Applications of Silicon Technology" by H M Mcconnell, J C Owicki, J W Parce, D L Miller, G T Baxter, H G Wada and S Pitchford in the Journal "Science", Volume 257, Sep. 25, 1992 describes a device which is capable of measuring the rate of proton excretion by cells in response to chemical/ligand stimulation. The Cytosensor device is based upon the fact that some cells acidify their surrounding environment because of acidic products of energy metabolism, especially glycolysis. The device measures changes in pH (acidification) that occur as cells release acidic metabolites into their immediate environment, this being related to rates of energy, metabolism. The Cytosensor may be used for two functions, that is as a detector for specific molecules (e.g. ligands) whereby responsive, viable cells in the instrument serve as detectors and amplifiers, and for the investigation of cell function and biochemistry. Thus the Cytosensor is a useful device for monitoring extra cellular pH which generally relates to changes in he energy metabolism of cells. However, there are many other electrochemical processes that cross the cell surface, some of which may contribute to the rate of acidification of the surrounding environment, but many others of which will not. Accordingly, it may be that in some circumstances a significant change in electrochemical activity within a cell does not result in significant change in the rate of acidification of the cell's environment.

The present invention provides a different method and device for assessing cell behaviour and metabolic activity. The present invention is based upon the realisation that the many chemical processes taking place at the cell surface produce electrochemical signals. The "signals" include, for example, potential noise and current noise, the term "noise" being used to indicate the sum of those signals resulting from cellular electrochemical activity. Techniques developed to assess the progress of electrical or electrochemical processes can be applied to the analysis of signals generated by the electrochemical activity of cells.

The present invention provides a method for assessing the metabolic and behavioural activities of cells, wherein electrochemical signals generated by the cells are detected and analysed to provide data representative of cell behaviour.

The term "behavioural activities" is used herein to include ionic transport and all those biological activities recognised as metabolic, proliferative, and locomotory, and cellular responses to exogenous factors.

The invention also provides an apparatus for assessing the metabolic and behavioural activities of cells, comprising a means for the detection of electrochemical signals generated by the cells, and means for analysing the detected signals to provide data reflecting cell behaviour and changes therein.

Cells maintained in vitro under defined culture conditions produce a characteristic electrochemical signal, this being modified upon exposure to one or more chemicals/ligands/biological factors know to affect cell activity. The electrochemical signals generated by cells with or without stimulation, upon analysis, provides a different set of data representative of the behavioural characteristics of those cells. Thus it is believed that a high degree of discrimination is afforded by analysis of the electrochemical processes which reflect, and relate, to modified cell behaviour.

The signals monitored and subsequently analysed, could be, for example. the electrochemical potential noise. Alternatively, fluctuations in electrochemical current may be monitored either separately, or in combination with the electrochemical potential.

The apparatus in accordance with the invention may comprise a container for receiving a culture medium containing a sample of cells to be assessed, the cells being supported by a chemically inert, electronically conductive surface arranged within the container. An electrochemical pathway in the form of a conducting medium within, for example, a tube and connected to a reference electrode may be arranged within the container in contact with the culture medium. The electrochemical noise detecting means is connected to the conductive surface and the reference electrode to detect electrochemical noise signals generated in the sample. The chemically inert conductive surface may be in the form of a film of gold formed, for example, as a foil or as a deposit on an electrically insulating substrate.

Embodiments of the present invention will now be described, by way of example, with reference to the accompanying drawings, in which.

Figure 1:
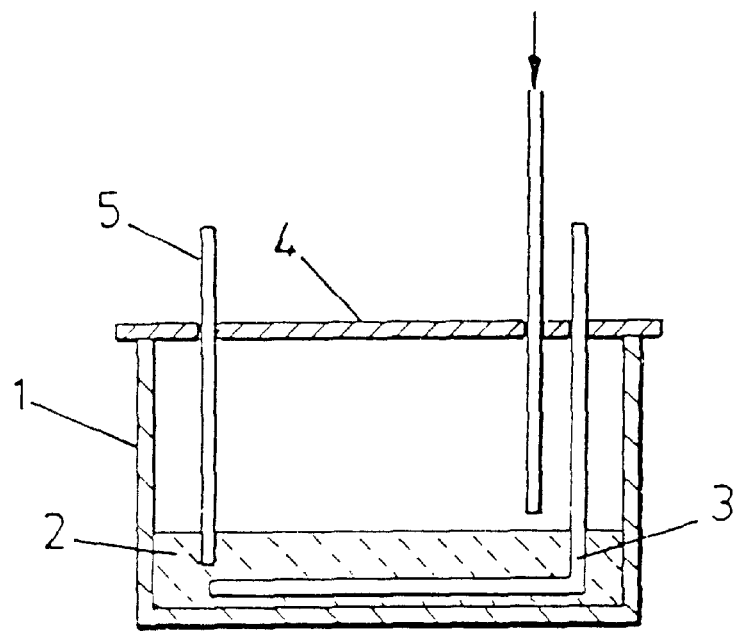
FIG. 1 is a schematic representation of an apparatus in accordance with the present invention.

Referring to FIG. 1, the illustrated apparatus comprises a container 1 into which culture medium 2 has been introduced. Located within the container and partially submerged by the medium is a main electrode 3, the surface of which is formed by a thin film of gold. This electrically conductive surface supports adherent, viable cells previously grown to near confluence. The container is closed by a lid 4 which is penetrated by a tube 5 filled with an electrochemically conducting medium that is in electrochemical contact with a reference electrode. The end of the tube 5 is immersed in the culture medium. A further tube is provided through which test factors such as stimulants or suppressants can be injected into the container.

Figure 2:
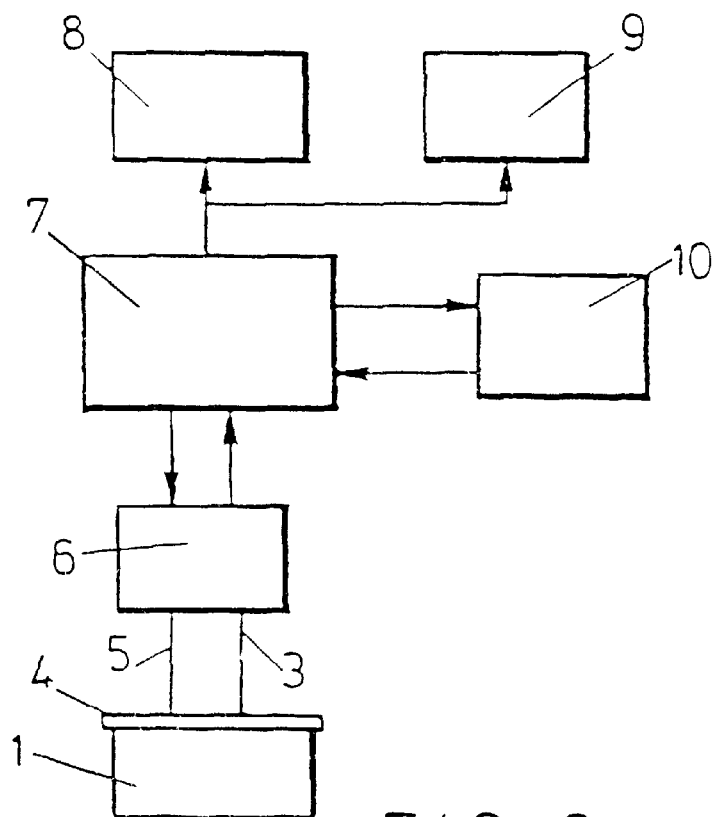
FIG. 2 is a schematic representation of an electrical circuit for analysing potential noise signals generated in the apparatus of FIG. 1.

Referring now to FIG. 2, reference numerals 1, 3, 4 and 5 are used for the same components as are identified by those numbers in FIG 1. A digital voltmeter 6 monitors the potential between electrodes 3 and 5 and the output of the digital voltmeter is applied to personal computer (PC) 7. The PC processes the voltmeter output to generate a signal which drives a display 8 and a hard copy printer 9. In addition, the PC processes the data to provide an output to a spectrum analyser 10.

Figure 3A:
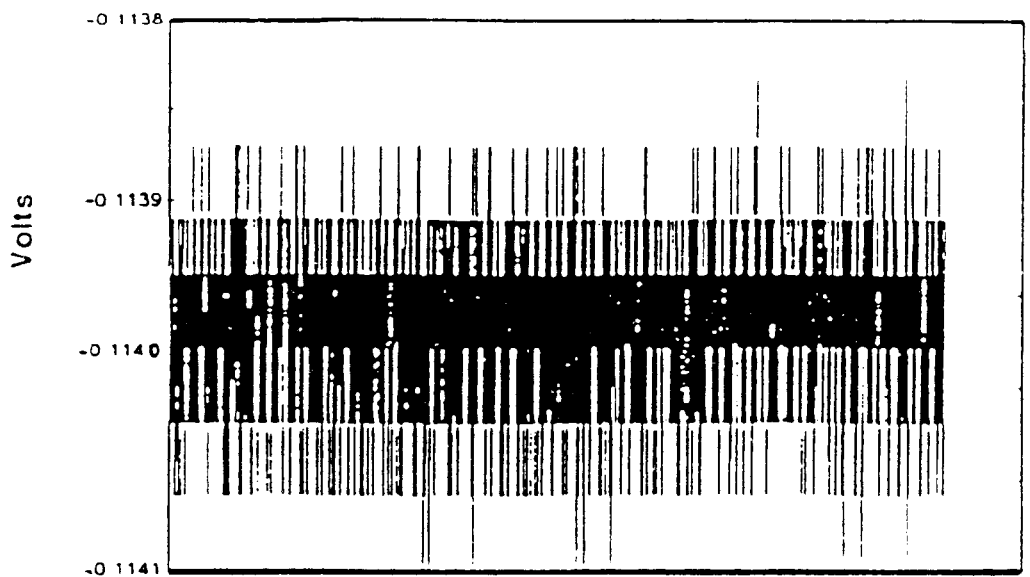
FIGS. 3a and 3b are plots of potential 'noise' against time generated by carcinoma cells and fibroblasts, respectively, using the apparatus of FIG. 1 and the circuit of FIG. 2.
Figure 3B:
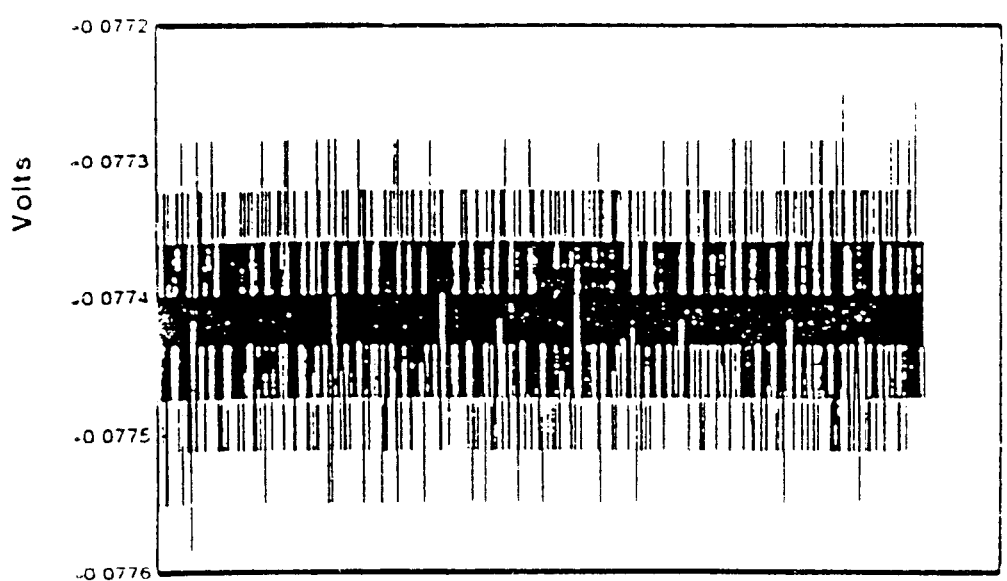

FIGS. 3a and 3b show results obtained using the apparatus illustrated in FIGS. 1 and 2, the results being represented by the rest potentials monitored against time for breast carcinoma cells (FIG. 3a) and human fibroblasts (FIG. 3b). To further illustrate the electrochemical differences which arise with different cells on the probe surface, the following table represents examples of the mean rest potential and standard deviation in the mean rest potential obtained for three cell types under similar culture conditions.

| Probe surface condition | Mean rest potential/ mv | standard deviation in rest potential/mv |
| --- | --- | --- |
| Bare (cell-free) | −61.1 | 11.1 |
| Cancer cell (BC 8701) | −129.6 | 10.7 |
| Fibroblast (HAC90 P2) | −95.6 | 5.2 |

Figure 4A:
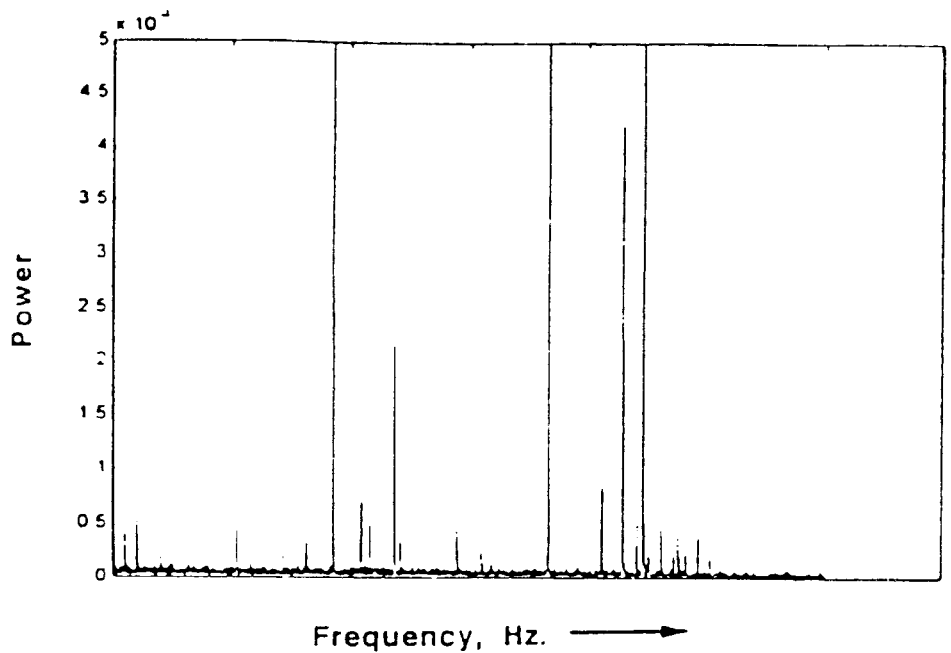
FIG. 4a is representation of a power spectrum associated with carcinoma cells produced on the basis of the information shown in FIG. 3a and subsequently analysed.
Figure 4B:
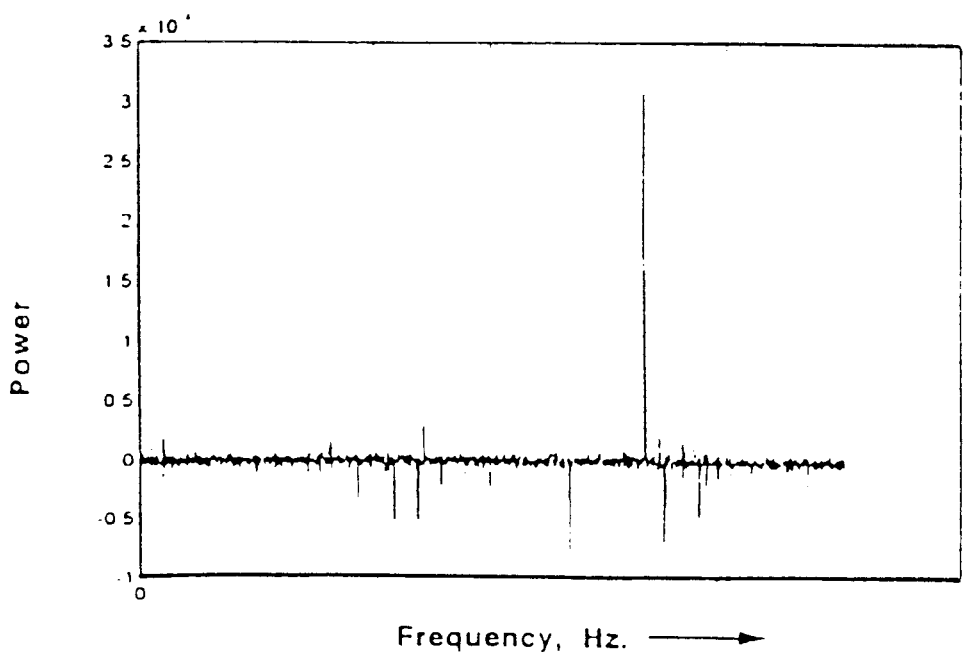
FIG. 4b illustrates differences in the power spectra of the two cell types that is breast carcinoma and fibroblasts.

FIG. 4a illustrates the power spectrum derived from analysis of the signals from the unstimulated breast carcinoma cells. FIG. 4b represents the power spectra differences observed for separate cultures of breast carcinoma cells and normal fibroblasts, to illustrate that different types of cell generate different electrochemical signals. Thus FIG. 4b represents the difference between the results shown in FIG. 4a for carcinoma cells and the equivalent results (not shown) for fibroblasts. In the absence of differences, the profile of FIG. 4b would approximate zero across the frequency range.

Figure 5:
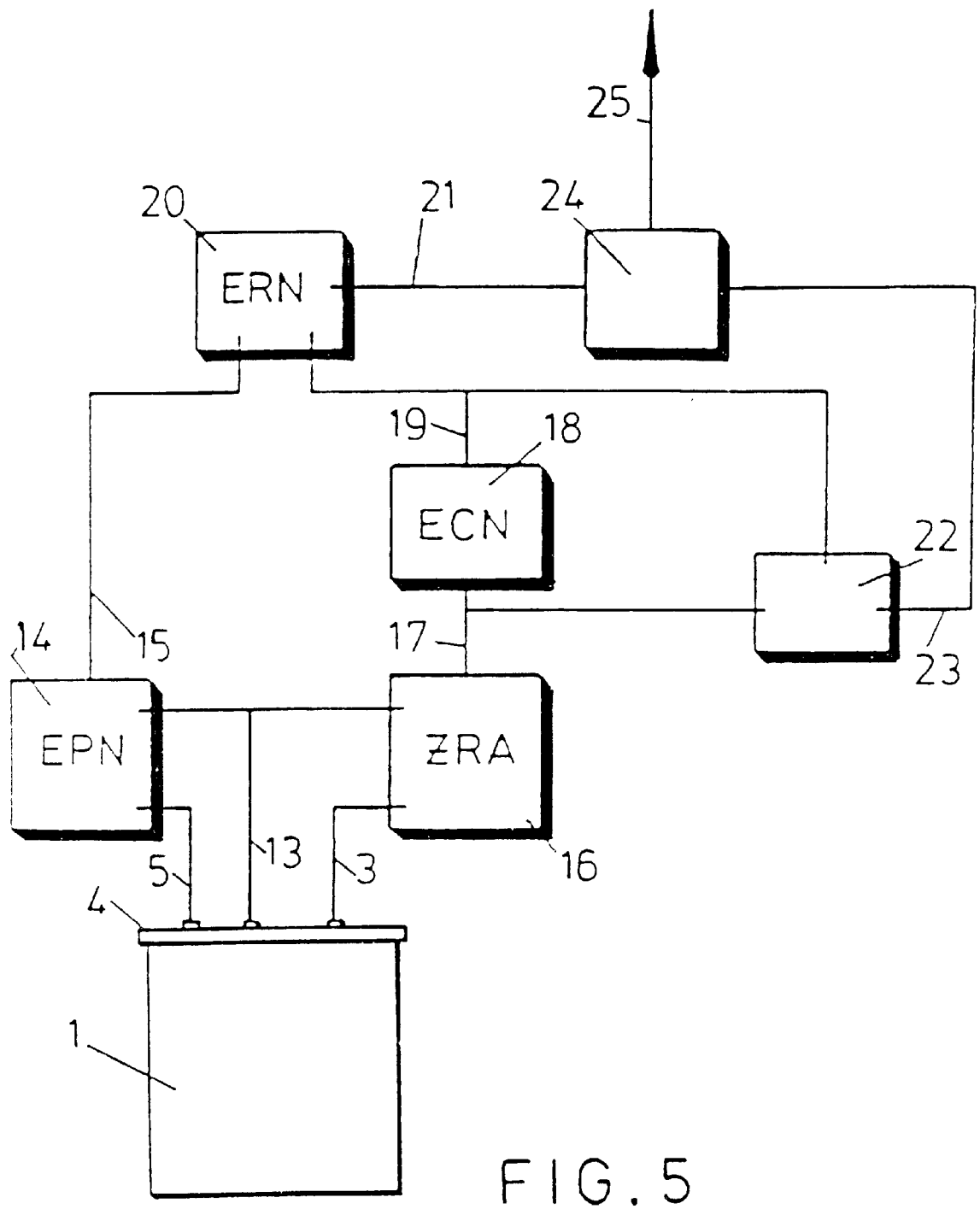
FIG. 5 is a schematic representation of circuitry which may be used to monitor electrochemical current noise signals generated using a modified form of the apparatus shown in FIG. 1.

As an alternative to monitoring fluctuations in electrochemical potential, it is possible to monitor fluctuations in electrochemical current. FIG. 5 schematically illustrates on arrangement for monitoring electrochemical current noise. As shown in FIG. 5, a third electrode 13 is introduced, this being partially immersed in the culture medium in exactly the same manner as electrode 5. Electrodes 5 and 13 are connected to an electrochemical potential noise monitoring apparatus 14 which provides on output 15 output signal representative of Vn, that is the rms or standard deviation of the potential noise signal. A zero resistance ammeter 16 is connected across electrodes 3 and 13 and produces on output 17 an output signal corresponding to lm, that is the dc coupling current.

The output 17 is connected to an electrochemical current noise measuring apparatus 18 which provides on output 19 an output signal corresponding to ln, that is the rms or standard deviation of the current noise signal. The outputs 15 and 19 are applied to a circuit 20 for comparing the electrochemical potential noise signal and the electrochemical current noise signal. The circuit 20 provides on output 21 an output signal Rn which represents impedance noise and is equal to Vn/ln. The output 21 is effectively indicative of the overall rate of electrochemical activity.

The structure illustrated in FIG. 5 provides effectively four outputs, each of which varies in a manner that is indicative of the rate and/or nature of the electrochemical activity of the cells to which the electrodes 3, 5 and 13 are exposed. It is believed that if a comparison is made between the signals appearing on outputs 17 and 19 important information can be gained as to the nature of the cell activity. Accordingly, a comparator circuit 22 is connected to the outputs 17 and 19 and provides on output 23 an output signal which is representative of lm/ln.

The output 23 results from the comparison of the meaning coupling current to the standard deviation values of the electrochemical current noise signal, and it is believed that this will provide information characteristic of the cell activity that generated the signal.

A further comparator 24 is provided to compare the output 21 with the output 23 to produce a still further output 25 which again is indicative of characteristic features of the electrochemical activity.

The arrangement of FIG. 5 enables the generation of a significant number of different signals all based on the same electrochemical activity. It is believed that different cell conditions which might result in, for example, similar fluctuations in electrochemical potential are unlikely to result in close similarity between the other available outputs. Thus the arrangement FIG. 5, improves the probability of being able to adequately discriminate between different cell behavioural patterns.

The apparatus illustrated in FIGS. 2 and 5 is very similar to that illustrated in European Patent Specification Nos. 0084404 and 0302073 respectively. Those patent specifications are concerned with the monitoring of corrosion but it is believed that the techniques developed for monitoring corrosion by reference to electrochemical noise are equally applicable to the analysis of electrochemical activity produced by cells. It will be appreciated that although FIGS. 2 and 5 show examples of possible apparatus for monitoring electrochemical signals, there are alternative arrangements available as will be appreciated by reference to the numerous academic and patent publications relating to for example the analysis of electrochemical noise generated within corroding materials. Further research is expected to enable specific cell and/or tissue behavioural activities to be correlated with associated and characteristic electrochemical signals. It is believed, however, that since all cellular biological activities are based on chemical processes and electrochemical reactions, the analysis of electrochemical signals generated by cells will give access to a large amount of data some of which relate to specific behavioral activities. For example, since stimulated or cancer cells invariably have a more active behaviour, such as elevated proliferative activity, it is very likely that the underlying chemical reactions taking place within such cells are different from those taking place in normal cells which provide more consistent functional activities. Thus each specific cell type is likely to have a unique "signature" of cell behaviour reflecting complex combinations of electrochemical reactions and those "signatures" should be accessible to an analysis of associated electrochemical signals.

In the experiments, illustrative results of which are represented in FIGS. 3 and 4 and Table 1, both the voltage responses and the associated power spectra for the metabolically active cancer cell culture and fibroblast culture were measurably different.

Figure 6:
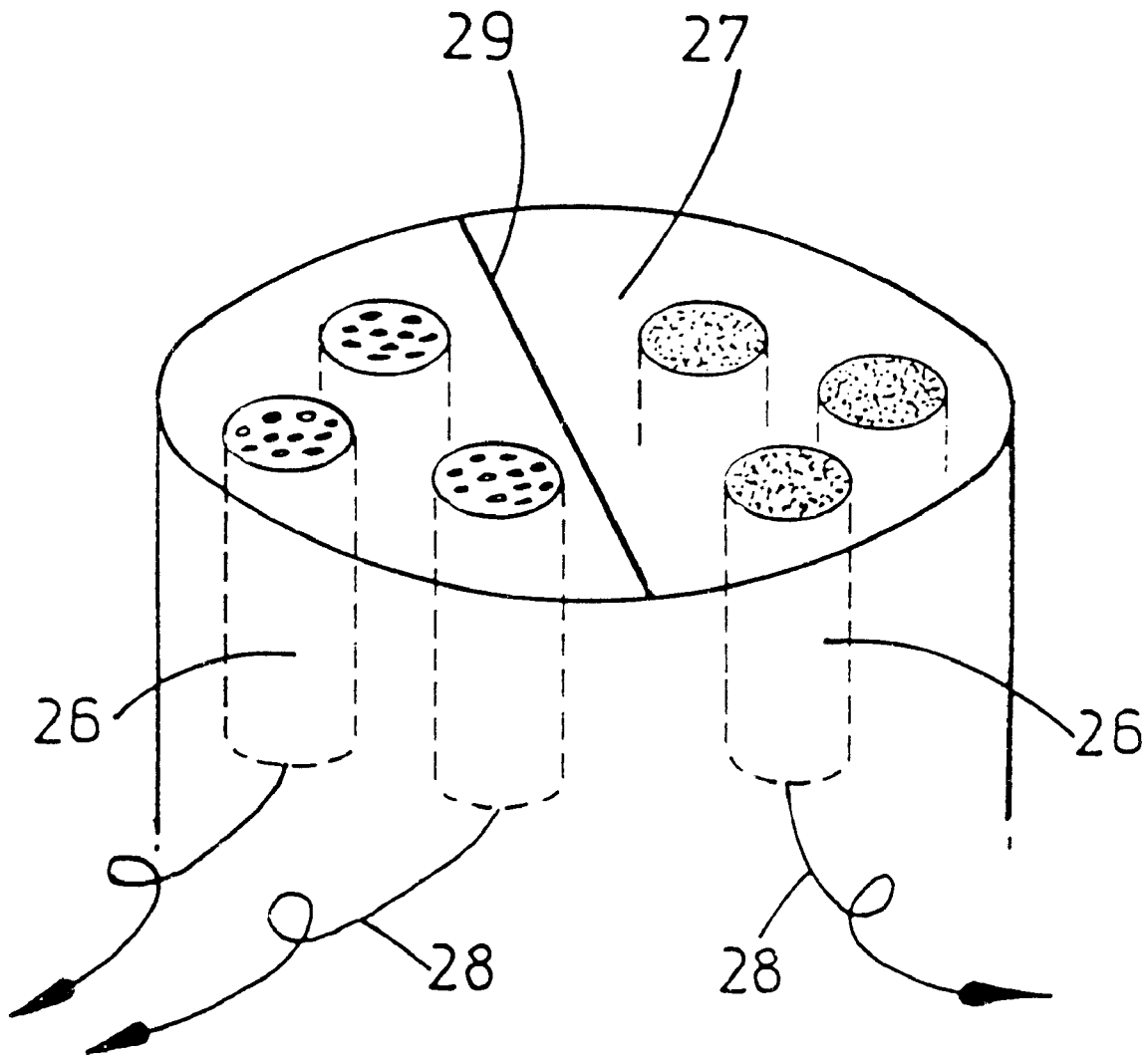
FIG. 6 illustrates a minaturised probe structure suitable for use in accordance wit the invention.

In order to improve the amount of data which can be obtained from a limited number of cells, and to enable the improvement of procedures, it is desirable to provide a miniaturised apparatus which is capable of providing more than one output for a single body of cells, and which is capable of providing control outputs representing background signals which may arise even in the absence of cells. FIG. 6 schematically illustrates one structure which can provide such capabilities.

The probe assembly of FIG. 6 comprises six metallic wires 26, which may be gold, embedded in an electrically insulating body 27 of for example cold curing or hot setting resin. The end surface of each of the wires is exposed so as to define an electrode surface onto which cells may be deposited. The surface of the body 27 on which the ends of the wires 26 are exposed may be polished using a lapidary wheel. Each of the six wires 26 is separately connected by a respective conductor 28 to a respective monitoring circuit (not shown). Thus independent outputs are provided for each of the six wires.

The wires 26 are arranged in two groups of three located on opposite sides of a notional line 29. The exposed ends of one of the groups (to the left of line 29 in FIG. 6) and the adjacent surface of the body 27 are placed in contact with the body of cells to be investigated. Some of the cells will become attached to the ends of the wires, such cells being represented by small circular areas in FIG. 6. The other group of wires 26 is cell free. Cells could be deposited in this manner by for example covering one group of wires and the adjacent body surface with an insulating layer of film, e.g. Parafilm, during the cell attachment process, and removing the film prior to monitoring cell activity.

FIG. 6 shows six wires 26 in total, but it will be appreciated that both the number and diameter of the wires may be adjusted to suite particular applications. Wire diameters of from 0.2 to 2.0 mm will be suitable in sonic circumstances.

The apparatus of FIG. 6 permits the monitoring of replicate electrodes, with and without cells attached, in a single culture apparatus. This provides improved consistency of data, convenience and simplicity compared to the use of separate culture units.

The investigation so far has been concerned with in vito studies. It is believed, however, that the present invention could be adapted and developed for use in vivo.

There are many potential applications for the present invention. For example, the invention enables the provision of an analytical tool for the study of specific cell behaviour in vitro, such as the effects of pharmaceutical compounds, hormones, cytokines, prostaglandins, mutagens etc on selected target cells, biocompatability screening, e.g. in vitro evaluation of prosthetic material surfaces for improvement of implant osseointegration; the identification of specific cell types in vivo, for example, detecting the presence of certain tumour cells and their location within specific tissues; the selection and optimisation of anti-cancer treatment in ex-vivo culture; and an assessment of brain activity and regional variations of such activity.

It will be appreciated that the present invention would for example, enable data to be captured in real time. Accordingly, the normally slow progress of investigations related to the effects of, for example, a particular chemical or factor on cell activity, can be transformed by the application of the present invention. Furthermore, given that the invention relies upon electrochemical signals generated by cell in vitro, ex vivo or in vivo, it is believed possible to identify particular cell types without inducing changes or modifications in their behaviour, that is without it being essential to stimulate or suppress specific cell activities. Further information can be obtained subsequently by stimulation or suppression of the same cells.

We claim:

1. A method of assessing the metabolic and behavioral activities of biological cells adhered to an electrode surface, comprising:

directly detecting at the cell surfaces the electrochemical signals generated by processes occurring at the cell surfaces, and analyzing fluctuations in the electrochemical signals generated at the electrode surface to provide data representative of cell behavior.

2. The method of claim 1, wherein the cells are grown on the electrode surface.

3. The method of claim 1, comprising:

exposing the cells to at least one exogenous factor which may affect cell activity, and monitoring any electrochemical response to the at least one exogenous factor by reference to the detected electrochemical signals.

4. The method of claim 1, wherein the cells are adhered to a chemically inert electrically conductive electrode surface immersed in a culture medium which is in electrical contact with a reference electrode, and the fluctuations in the electrochemical signals are detected by connecting an electrochemical signal detector between the electrically conductive electrode surface and the reference electrode.

5. The method of claim 4, wherein fluctuations in electrochemical potential between the conductive surface and the reference electrode are detected and analyzed.

6. The method of claim 1, wherein fluctuations in electrochemical current between two electrically conductive electrodes, at least one of which is in direct contact with the cell surfaces are detected and analyzed.

7. A method for assessing the metabolic and behavioral activities of biological cells, comprising:

attaching the cells to a chemically inert electrically conductive surface immersed in a culture medium which is in electrical contact with a reference electrode, directly detecting electrochemical signals generated between the electrically conductive surface and the reference electrode by processes occurring at the cell surfaces, and analyzing fluctuations in the detected signals generated at the electrode surface to provide data representative of cell behavior.

8. A method for assessing the metabolic and behavioral activities of biological cells, comprising:

placing the cells in contact with an electrically conductive electrode such that electrochemical signals generated at surfaces of the cells which are in contact with the electrode are directly applied to the electrode, detecting the signals applied to the electrode by the cell surfaces in contact with the electrode, and analyzing fluctuations in the detected signals generated at the electrode surface to provide data representative of cell behavior.

9. An apparatus for assessing the metabolic and behavioral activities of biological cells, comprising:

means for receiving the cells such that the cells are in electrical contact with an electrically conductive surface, detecting means for directly detecting electrochemical signals generated by processes occurring at surfaces of the cells in contact with the conductive surface, and analyzing fluctuations in means for analyzing the detected signals generated at the electrode surface to provide data representative of cell behavior.

10. The apparatus of claim 9, wherein the means for receiving a culture medium containing the sample of cells to be assessed is a container containing a chemically inert electrically conductive surface and a reference electrode arranged therein so as to contact the culture medium, and wherein the detecting means is connected between said electrically conductive surface and said reference electrode.

11. The apparatus of claim 10, wherein said electrically conductive surface comprises a conductive film formed on an electrically insulating substrate.

12. The apparatus of claim 11, wherein said electrically conductive surface comprises at least one wire extending through and to the surface of an insulating body.

13. The apparatus of claim 12, comprising a plurality of wires, each of the plurality of wires extending through and to the surface of the insulting body and each of the plurality of wires being connected to a respective detecting means.

14. The apparatus of claim 9, wherein the detecting means detects fluctuations in electrochemical potential.

15. The apparatus of claim 9, wherein the detecting means detects fluctuations in electrochemical current.

* * * * *